United States Patent [19]

Gozzo et al.

[11] 4,400,517
[45] Aug. 23, 1983

[54] PHOSPHORIC ESTERS DERIVED FROM 1,2,4-TRIAZOLE HAVING AN INSECTICIDAL, NEMATOCIDAL AND ACARICIDAL ACTION, AND THEIR PREPARATION

[75] Inventors: Franco Gozzo, S. Donato Milanese; Pier M. Boschi, Piacenza; Angelo Longoni, Milan, all of Italy

[73] Assignee: Montedison S.p.A., Milan, Italy

[21] Appl. No.: 116,547

[22] Filed: Jan. 29, 1980

Related U.S. Application Data

[63] Continuation-in-part of Ser. No. 851,202, Nov. 14, 1977, Pat. No. 4,220,789.

[30] Foreign Application Priority Data

Nov. 17, 1976 [IT]  Italy .............................. 29420 A/76
Mar. 3, 1977 [IT]  Italy .............................. 20855 A/76

[51] Int. Cl.$^3$ ..................... A01N 57/16; A01N 57/24; A01N 57/32; C07F 9/65
[52] U.S. Cl. ............................ 548/118; 260/453.1; 260/543.2; 424/200; 548/263; 548/265; 542/458; 560/219; 560/225; 560/226; 560/251; 564/19; 564/20; 564/36
[58] Field of Search ....................... 424/200; 548/118; 542/458

[56] References Cited

U.S. PATENT DOCUMENTS 3,862,124  1/1975  Dawes et al. ..................... 548/118

FOREIGN PATENT DOCUMENTS 2750813  5/1978  Fed. Rep. of Germany ...... 424/200
713278  8/1954  United Kingdom ................ 548/118

*Primary Examiner*—Alton D. Rollins
*Attorney, Agent, or Firm*—Stevens, Davis, Miller & Mosher

[57] ABSTRACT

1,2,4-triazol-(5)-yl-[thio] phosphates are disclosed having the formula wherein
$R^1$ = alkyl with from 1 to 5 carbon atoms;
$R^2$ = $OR^1$, $R^1$, $C_6H_5$, $NHR^1$, $N(R^1)_2$;
X = O, S
$R^3$ = H, alkyl with from 1 to 5 carbon atoms, $C_6H_5$, benzyl, alkenyl with from 2 to 6 carbon atoms, alkynyl with from 2 to 6 carbon atoms; and
$R^4$ = vinyl, halovinyl, polyhalovinyl, vinyl substituted with aryl groups, alkyl groups with from 1 to 4 carbon atoms, O-alkyl groups with from 1 to 4 carbon atoms, S-alkyl groups with from 1 to 4 carbon atoms; haloalkyl, acetyl, cyclohexenyl, benzoyl $$-\underset{CH_3}{\underset{|}{CH}}-R^5 \text{ [wherein } R^5 = OH, O-\underset{O}{\underset{\|}{C}}-R^1, O-\underset{O}{\underset{\|}{C}}-\text{vinyl}$$

$$O-\underset{O}{\underset{\|}{C}}-(\text{poly})\text{-halovinyl}, O-\underset{O}{\underset{\|}{C}}-\text{haloalkyl}, Cl, SR^1,$$

$$OR^1, N(R^1)_2, NHR^1],$$

$$-CO-CH_2-SR^1, -\underset{R^5}{\underset{|}{CH}}-CH_2SR^1$$

Also disclosed are 1,2,4-triazole intermediates having the formula wherein: X, $R^3$ and $R^4$ have the same meanings as indicated above. The phosphate esters are useful in combatting infestations of pests such as orthoptera, aphides, diptera, lepidoptera, coleoptera, acari, nematodes.

14 Claims, No Drawings

PHOSPHORIC ESTERS DERIVED FROM 1,2,4-TRIAZOLE HAVING AN INSECTICIDAL, NEMATOCIDAL AND ACARICIDAL ACTION, AND THEIR PREPARATION

This application is a continuation-in-part of our prior copending application Ser. No. 851,202, filed Nov. 14, 1977, now U.S. Pat. No. 4,220,789, granted Sept. 7, 1980.

The present invention relates to new esters containing phosphorus in their acid part, and which are derived from 5-hydroxy (or 5-mercapto-)-1,2,4-triazoles. More particularly, this invention relates to esters of pentavalent phosphorous derived from new 5-hydroxy (or 5-mercapto)-1,2,4-triazoles substituted or unsubstituted in position 1 and substituted in position 3 of their nucleus. The invention also relates to methods for their preparation, their use in combatting pests such as orthoptera, aphides, diptera, coleoptera, lepidoptera, acari and nematoda.

Amongst the thiophosphates derived from 3-hydroxy-1,2,4-triazole variously substituted in positions 1 and 5 of the ring, many have proved to develop an insecticidal activity. Amongst these, two products have been commercialized for the fight against insect pests:

Triazophos:

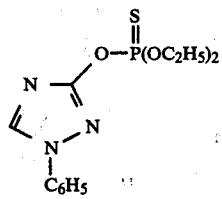

an insecticide which acts by contact and ingestion, commercialized by the HOECHST Company and described in South African Pat. No. 6.803.471; and Diethyl-(1-isopropyl-5-chloro-1,2,4-triazole-3-yl) phosphoro-thionate (Miral)® produced by 'Ciba-Geigy':

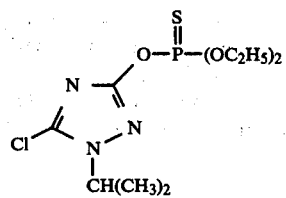

and described in German Pat. No. 2,260,015, and which is effective against insects in the soil.

Lesser attention has been given to the derivatives of 5-hydroxy-1,2,4-triazole, such as diethoxy-phosphorothioate of 1-methyl-3-phenyl-5-hydroxy-1,2,4-triazole of the formula:

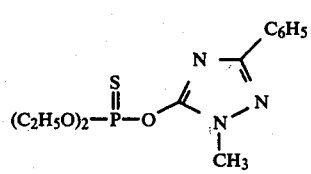

claimed in U.S. Pat. No. 3,689,500.

We have now found that esters of pentavalent phosphorus of the general formula (I):

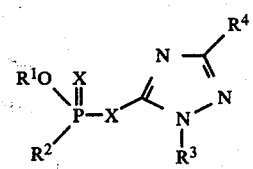

wherein:
$R^1$ = alkyl with from 1 to 5 carbon atoms;
$R^2$ = $OR^1$, $R^1$, $C_6H_5$, $NHR^1$, $N(R^1)_2$;
X = O, S;
$R^3$ = H, alkyls with from 1 to 5 carbon atoms, $C_6H_5$, benzyl, alkenyl with from 2 to 6 carbon atoms, alkynyl with from 2 to 6 carbon atoms; and
$R^4$ = halovinyl, polyhalovinyl, vinyl, vinyl substituted with aryl groups, alkyl groups with $C_1$–$C_4$, O-alkyl groups with $C_1$–$C_4$, and S-alkyl groups with $C_1$–$C_4$; haloalkyl, acetyl, cyclohexenyl, benzoyl,

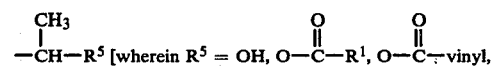

[wherein $R^5$ = OH, $O-C-R^1$, $O-C-$vinyl,

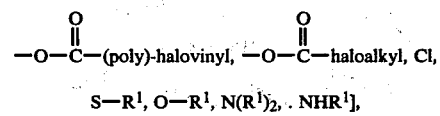

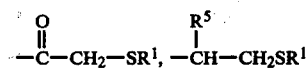

exert an insecticidal action over a wide action spectrum, since they are very active against orthoptera, aphides, diptera, coleoptera, lepidoptera, developing as well an acaricidal and nematocidal action, and at the same time having a low toxicity for warm-blooded animals. In some of the most active compounds according to the present invention, this toxicity is far much lower than that of Triazophos or analogous commercial compounds.

The derivatives of 5-hydroxy (or 5-mercapto)-1,2,4-triazole, in which $R^3$ is a phenyl, are prepared starting from the αchloro αsubstituted formylidenphenylhydrazines described in Italian Pat. No. 998,314. By treatment with ammonia and subsequently condensing the resulting amino-derivative with phosgene or thiophosgene, according to the reactions:

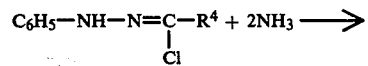

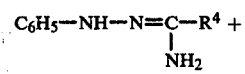

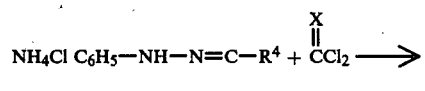

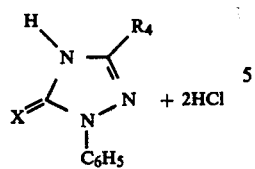

one obtains the desired triazole which, in an alkaline medium, is converted to the salt.

In the cases where $R^4$ contains a functional group, it is possible to exploit various reactions per se well known in organic chemistry for introducting other groups into the side chain of the triazol-one (or thione) itself (see Ex. 6 below). Thus, from 1-phenyl-3-acetyl-1,2,4-triazol-5-one, by exploiting the typical properties of the acetyl group, by reduction of the CO group, there was prepared the corresponding alcohol which, by treatment with thionyl chloride, allowed the preparation of the following compounds:

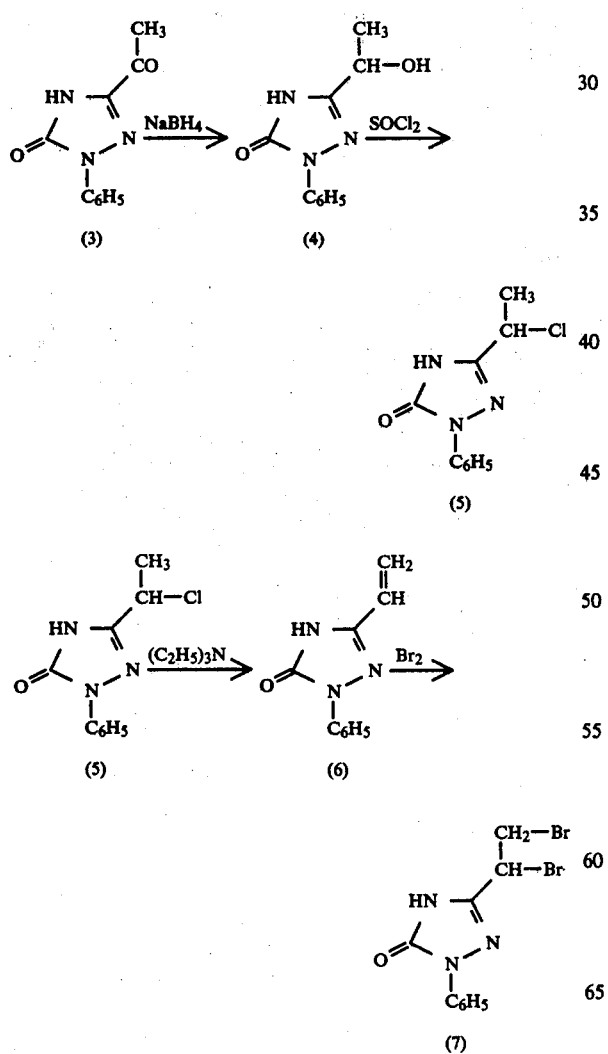

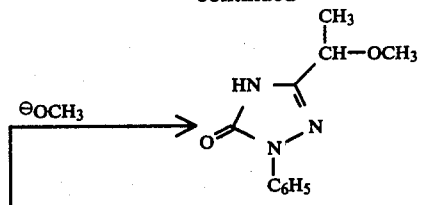

(8)

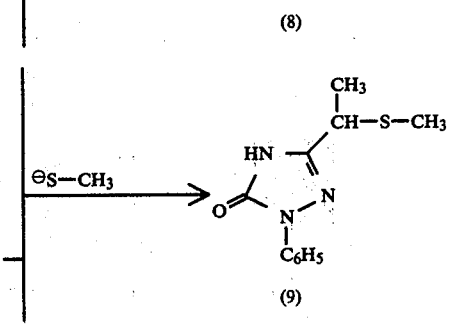

(9)

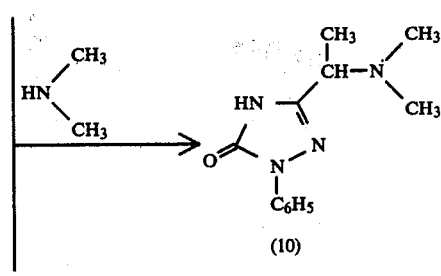

(10)

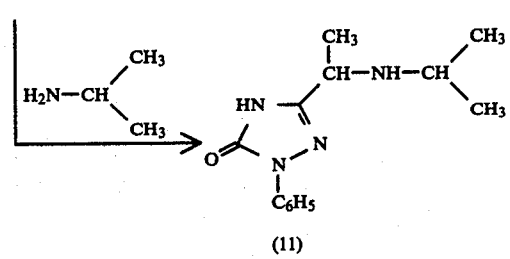

(11)

The triazoles in which $R^3$ is an alkyl have been prepared by condensing an aldehyde $R^4$—CHO with 2-alkyl-(thio)-semicarbazide, followed by treatment of the (thio)-semicarbazone thus obtained with bromine in glacial acetic acid in order to obtain the triazole which, in its turn, is treated in an alkaline medium as previously described, according to the reactions:

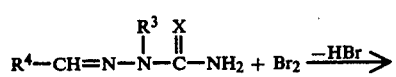

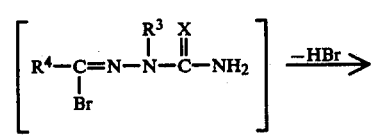

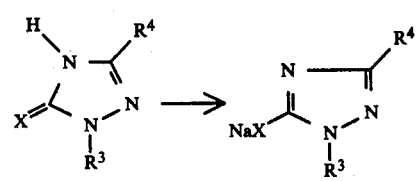

The (supposed) mechanism of the above-described reactions is reported in Tetrahedron Letters 28 (1971) on pages 2669 and following, in the cases in which $R^4$=aryl and X=O.

We have now found that if, on the contrary, $R^4$ is a vinyl group, this latter may also be attacked by bromine, giving place to a sequence of addition and elimination reactions. More particularly, when the starting aldehyde contains halogen atoms different from bromine in β position, these may be substituted by bromine atoms during the cyclization reaction through a possible sequence of stages, as hereunder indicated purely for exemplification:

tures of products containing bromine atoms in the vinylic positions of the derived triazole, as evidenced by Examples 8 and 9 below.

The vinyl group may also be introduced into position 3 of a 1-phenyl-1,2,4-triazole(5)-one (or thione) by starting from 1-phenyl-3-acetyl-1,2,4-triazole-5-one (or thione), as described in the first sequence of reactions performed on an acetyl group (see page 5, compound (6)).

Moreover, we have found that the cyclization of the semicarbazones of the general formula:

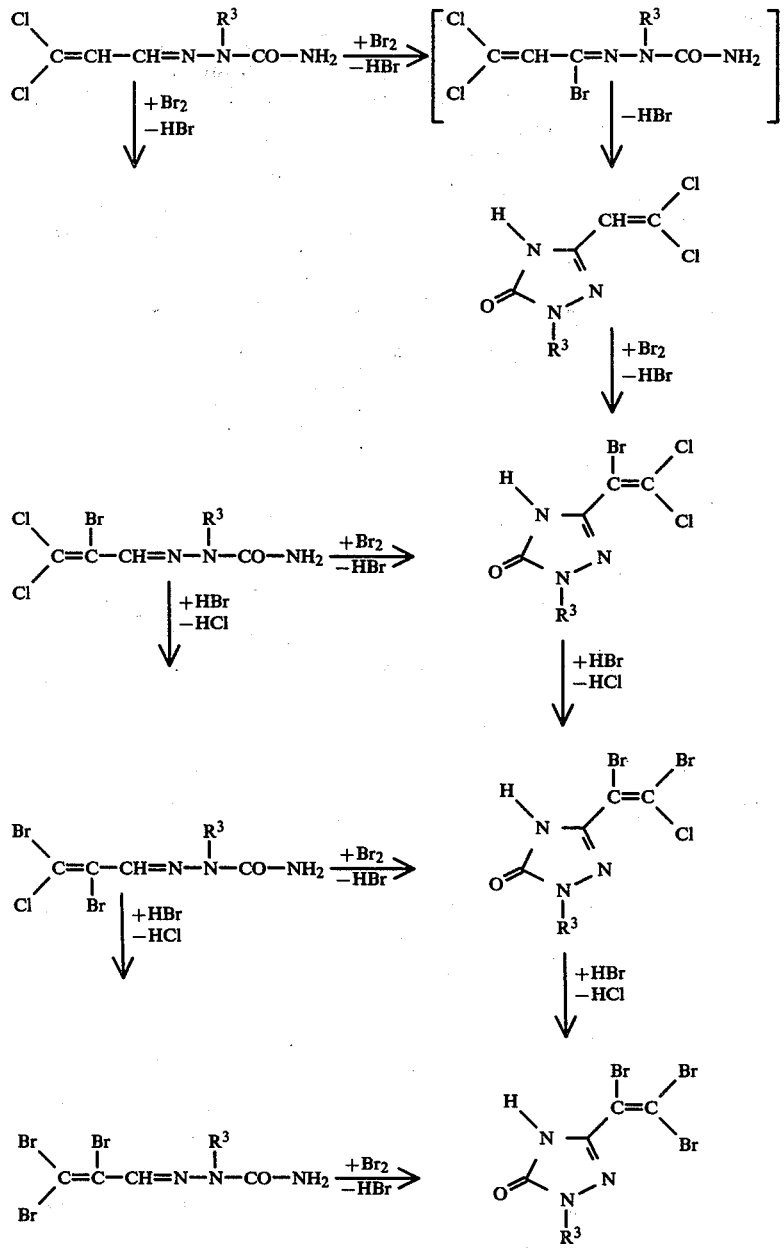

Depending on the temperature conditions, the reaction may be oriented (directed) towards the formation predominately of one single cyclization product containing the same (halo) vinylic group of the starting aldehyde, or towards the formation of products or mix-

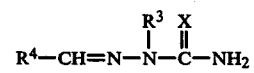

wherein:
R³=H; alkyl with from 1 to 5 carbon atoms; C₆H₅, benzyl, alkenyl, alkynyl;
R⁴=halovinyl, polyhalovinyl, vinyl, vinyl substituted with aryl, alkyl, O-alkyl, S-alkyl; haloalkyl, cyclohexenyl, acetyl, benzoyl groups;

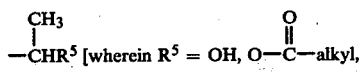

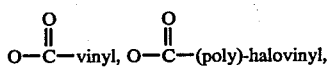

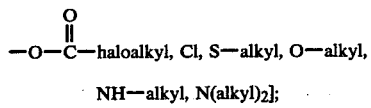

NH—alkyl, N(alkyl)₂];

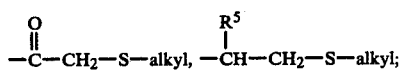

X=O, S may be carried out in the presence of the ferric chloride according to the reaction:

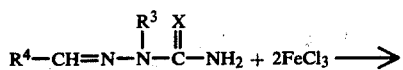

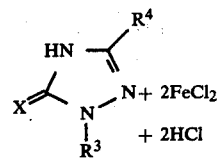

The cyclization reaction herein described allows on to obtain directly the triazolone (or thione) in a state of high purity even in cases wherein the R⁴ group contains olefinic double bonds that may be attacked by bromine, and so proves to be superior to the other methods described above.

The reaction is carried out in a polar solvent, preferably acetic acid, at boiling temperature.

The characteristics of the 1,2,4-triazol-5-ones prepared by one of the above described methods, are reported in Table 1.

TABLE 1

1,2,4 triazol-5-ones prepared by means of the processes described in the present invention and having the general formula:

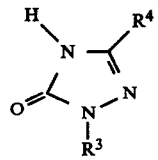

| Identification mark M | R³ | R⁴ | m.p. (°C.) (*) | Elemental analysis C theor. | C found | N theor. | N found |
|---|---|---|---|---|---|---|---|
| 7476 | C₆H₅ | COCH₃ | 174–6 | | | 20.68 | 20.57 |
| 7478 | C₆H₅ | COC₆H₅ | 220–1 | | | 15.84 | 16.03 |
| 8262 | C₆H₅ | CH—CH₃<br>   \|<br>  OH | 149–50 | | | 20.47 | 20.08 |
| 8085 | C₆H₅ | CH—CH₃<br>   \|<br>  Cl | 159–60 | | | 18.78 | 18.77 |
| 8263 | C₆H₅ | CH=CH₂ | 200 | | | 22.44 | 22.35 |
| 8264 | C₆H₅ | CH—CH₂Br<br>   \|<br>  Br | 177–8 | | | 12.11 | 11.47 |
| 8265 | C₆H₅ | CH—CH₃<br>   \|<br>  OCH₃ | 140–1 | | | 19.16 | 19.10 |
| 8266 | C₆H₅ | CH—CH₃<br>   \|<br>  SCH₃ | 130–2 | | | 17.70 | 17.23 |
| 8268 | C₆H₅ | CH—CH₃<br>   \|<br>  N(CH₃)₂.HCl | — | | | 20.85 | 20.56 |
| 8267 | C₆H₅ | CH—CH₃<br>   \|<br>  NH—CH(CH₃)₂ | 140–2 | | | 22.75 | 22.57 |
| 8269 | C₆H₅ | CO—CH₂—S—CH₃ | 189–90 | | | 16.85 | 16.76 |

TABLE 1-continued 1,2,4 triazol-5-ones prepared by means of the processes described in the present invention and having the general formula:

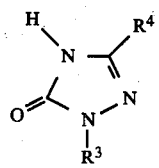

| Identification mark M | $R^3$ | $R^4$ | m.p. (°C.) (*) | Elemental analysis C theor. | found | N theor. | found |
|---|---|---|---|---|---|---|---|
| 8254 | $C_6H_5$ | CH—$CH_2$—S—$CH_3$ <br> \| <br> $CH_3$ | 102–4 | | | 16.72 | 16.39 |
| 8256 | $C_6H_5$ | CH—$CH_2$—S—$CH_3$ <br> \| <br> Cl | 145–6 | | | 15.58 | 15.35 |
| 8255 | $C_6H_5$ | $COOC_2H_5$ | 195–6 | | | 18.02 | 17.76 |
| 8258 | $C_6H_5$ | $CH_2OH$ | 178–80 | | | 21.48 | 22.20 |
| 8259 | $C_6H_5$ | $CH_2Cl$ | 154–6 | | | 20.04 | 19.90 |
| 8260 | $C_6H_5$ | $CH_2$—$OCH_3$ | 126–8 | | | 20.47 | 20.15 |
| 8270 | $C_6H_5$ | CHO | 164–6 | | | 22.21 | 21.57 |
| 8309 | $CH_3$ <br> $CH_3$ | C=C(Br)(Br)/Br <br> C=C(Cl)(Cl)/Br | 151–3 | | | 13.71 (mixture: 44% + 56%) | 13.74 |
| 8088 | $CH_3$ | C=C(Br)/Br,Br | 181–4 | | | 11.61 | 12.13 |
| 8310 | $CH_3$ | CH=C(Cl)/Cl | 215–6 | | | 21.65 | 21.66 |
| 8307 | $CH_3$ | CH=C(Br)/Br | 211–4 | | | 14.85 | 13.99 |
| | $CH_3$ | $CH=CH_2$ | 161–2 | 47.99 | 47.92 | 33.58 | 33.35 |
| | $CH_3$ | CH=CH—$CH_3$ | 167–8 | 51.79 | 50.91 | 30.19 | 30.01 |
| | $CH_3$ | CH=C($CH_3$)$_2$ | 144–6 | 54.88 | 56.27 | 27.40 | 28.54 |
| | $CH_3$ | C($CH_3$)=$CH_2$ | 168–9 | 51.79 | 50.85 | 30.19 | 29.33 |
| | $CH_3$ | C($CH_3$)=$CCl_2$ | 197–8 | 34.64 | 34.87 | 20.20 | 20.12 |
| | $CH_3$ | C(Cl)=$CCl_2$ | 201–2 | 26.29 | 26.64 | 18.40 | 18.42 |
| | $CH_3$ | CH=C($OCH_3$)Cl | 198–9 | 38.00 | 37.62 | 22.16 | 22.15 |
| | $CH_3$ | C(Br)=CH—$CH_3$ | 188–9 | 33.05 | 33.96 | 19.27 | 19.38 |
| | $CH_3$ | C(Cl)=CH—$CH_3$ | 191–2 | 41.51 | 40.89 | 24.20 | 23.49 |
| | $CH_3$ | C($C_2H_5$)=CH <br> \| <br> $C_3H_7$ | 146–7 | 61.51 | 61.69 | 21.52 | 21.74 |
| | CH($CH_3$)$_2$ | CH=$CCl_2$ | 164–5 | 37.86 | 38.70 | 18.92 | 19.30 |
| | ($CH_2$)$_3$—$CH_3$ | CH=$CCl_2$ | 107–8 | 40.70 | 40.73 | 17.80 | 17.90 |
| | ($CH_2$)$_3$—$CH_3$ | CH=CH—$CH_3$ | 90–1 | 59.64 | 58.82 | 23.18 | 23.04 |
| | $CH_2$—CH($CH_3$)$_2$ | CH=$CCl_2$ | 172–3 | 40.69 | 41.69 | 17.79 | 18.25 |

(*) The melting points are not corrected.

The 1,2,4-triazol-(5)-ones (or thiones) in the presence of a base are converted into their alkaline salts which, by reacting with suitable (thio)-phosphoryl chloride, give the triazolyl-(thio)-phosphate of the general formula (I):

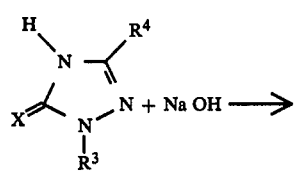
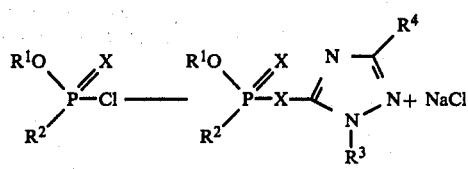

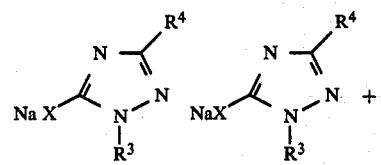

According to this procedure, the O,O-dialkyl-O-(1-$R^3$-3-$R^4$-1,2,4-triazol-5-yl)-thiophosphates reported in Table 2 were prepared:

TABLE 2

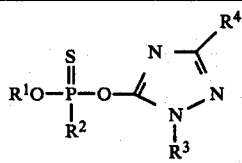

| Identification Mark M | $R^1$ | $R^2$ | $R^3$ | $R^4$ | C theor | C found | H theor | H found | N theor | N found | S theor | S found |
|---|---|---|---|---|---|---|---|---|---|---|---|---|
| 7490 | $C_2H_5$ | $OC_2H_5$ | $C_6H_5$ | CO—$C_6H_5$ | 54.6 | 53.6 | 4.8 | 4.6 | 10 | 9.9 | 7.69 | 8.00 |
| 7650 | $C_2H_5$ | $OC_2H_5$ | $C_6H_5$ | CO—$CH_3$ | 47.3 | 46.8 | 5.1 | 5.0 | 11.8 | 11.4 | 9.0 | 9.1 |
| 7852 Mixture 44% + 56% see ex. 8 | $C_2H_5$ / $C_2H_5$ | $OC_2H_5$ / $OC_2H_5$ | $CH_3$ / $CH_3$ | C(Br)=$CBr_2$ / C(Br)=$CCl_2$ | 23.3 | 24.6 | 2.8 | 2.9 | 9 | 9.1 | 6.9 | 6.9 |
| 7853 | $C_2H_5$ | $OC_2H_5$ | $C_6H_5$ | CH—$CH_3$ \| OH | 47.1 | 47.1 | 5.6 | 5.8 | 11.7 | 10.2 | 8.9 | 8.4 |
| 8084 | $C_2H_5$ | $OC_2H_5$ | $C_6H_5$ | CH—$CH_3$ \| $OCOCH_3$ | 48.1 | 48.1 | 5.6 | 5.5 | 10.5 | 10.8 | 8 | 7.7 |
| 8086 | $C_2H_5$ | $OC_2H_5$ | $C_6H_5$ | CH—$CH_3$ \| O—CO—CH=$CCl_2$ | 42.5 | 38.8 | 4.1 | 3.9 | 8.7 | 7.1 | 6.6 | 5.6 |
| 8086 | $C_2H_5$ | $OC_2H_5$ | $C_6H_5$ | CH—$CH_3$ \| O—CO—CH=$CCl_2$ | 42.5 | 38.8 | 4.1 | 3.9 | 8.7 | 7.1 | 6.6 | 5.6 |
| 8089 | $C_2H_5$ | $OC_2H_5$ | $CH_3$ | C(Br)=$CBr_2$ | 21.1 | 21.5 | 2.6 | 2.5 | 8.2 | 8.1 | 6.2 | 6.5 |
| 8167 | $C_2H_5$ | $OC_2H_5$ | $C_6H_5$ | CH—$CH_3$ \| $OCH_3$ | 48.5 | 48.4 | 6.0 | 5.9 | 11.3 | 11.4 | 8.6 | 8.3 |
| 8169 | $C_2H_5$ | $OC_2H_5$ | $C_6H_5$ | CO—$CH_2SCH_3$ | 44.9 | 45.2 | 5.0 | 5.1 | 10.5 | 10.5 | 16.0 | 15.0 |
| 8170 | $C_2H_5$ | $OC_2H_5$ | $C_6H_5$ | CH—$CH_3$ \| S—$CH_3$ | 46.5 | 45.8 | 5.7 | 5.7 | 10.8 | 10.6 | 16.6 | 15.5 |
| 8171 | $C_2H_5$ | $OC_2H_5$ | $C_6H_5$ | CH—$CH_3$ \| $N(CH_3)_2$ | 49.9 | 48.8 | 6.6 | 7.0 | 14.6 | 13.4 | 8.3 | 7.3 |
| 8173 | $C_2H_5$ | $OC_2H_5$ | $C_6H_5$ | CH—$CH_2$—$SCH_3$ \| OH | 44.6 | 43.1 | 5.5 | 5.5 | 10.4 | 10.4 | 15.9 | 14.0 |
| 8174 | $C_2H_5$ | $OC_2H_5$ | $CH_3$ | CH=$CCl_2$ | 31.2 | 29.1 | 4.1 | 3.8 | 12.1 | 11.0 | 9.2 | 7.6 |
| 8257 | $C_2H_5$ | $OC_2H_5$ | $C_6H_5$ | $COOC_2H_5$ | 46.8 | 47.3 | 5.2 | 5.3 | 10.9 | 11.0 | 8.3 | 7.8 |
| 8261 | $C_2H_5$ | $OC_2H_5$ | $C_6H_5$ | CH=$CH_2$ | 49.5 | 48.5 | 5.3 | 5.4 | 12.4 | 12.8 | 9.4 | 8.4 |

TABLE 2-continued $$R^1O-\underset{\underset{R^2}{|}}{\overset{\overset{S}{||}}{P}}-O-\underset{}{\overset{}{C}}=\underset{\underset{\underset{R^3}{|}}{N}}{N}-\overset{R^4}{\underset{}{C}}$$

| Identification Mark M | $R^1$ | $R^2$ | $R^3$ | $R^4$ | ELEMENTAL ANALYSIS | | | | | | | |
|---|---|---|---|---|---|---|---|---|---|---|---|---|
| | | | | | C | | H | | N | | S | |
| | | | | | theor | found | theor | found | theor | found | theor | found |
| 8308 | $C_2H_5$ | $OC_2H_5$ | $CH_3$ | $CH=CBr_2$ | 24.8 | 25.5 | 3.2 | 3.2 | 9.7 | 10.2 | 7.4 | 7.0 |
| 8550 | $C_2H_5$ | $OC_2H_5$ | $CH_3$ | $C(CH_3)=CCl_2$ | 33.34 | 33.34 | | | 11.66 | 11.55 | 8.90 | 8.33 |
| 8559 | $C_2H_5$ | $C_2H_5$ | $CH_3$ | $CH=CCl_2$ | 32.74 | 33.58 | | | 12.73 | 12.83 | 9.71 | 8.81 |
| 8560 | $C_2H_5$ | $OC_2H_5$ | $CH_3$ | $C(Cl)=CCl_2$ | 28.4 | 28.62 | | | 11.04 | 11.05 | 8.42 | 7.71 |
| 8448 | $n-C_3H_7$ | $O-n-C_3H_7$ | $CH_3$ | $CH=CCl_2$ | 35.30 | 34.85 | | | 11.22 | 10.90 | 8.57 | 8.09 |
| 8593 | $C_2H_5$ | $OC_2H_5$ | $CH_3$ | $C(CH_3)=CH_2$ | 41.23 | 42.34 | | | 14.94 | 14.67 | 11.01 | 10.14 |
| 8592 | $C_2H_5$ | $OC_2H_5$ | $CH_3$ | $CH=C(OCH_3)Cl$ | 35.14 | 35.12 | | | 12.30 | 12.32 | 9.38 | 9.02 |
| 8476 | $C_2H_5$ | $OC_2H_5$ | $CH_3$ | $CH=CH_2$ | 39.98 | 36.45 | | | 15.15 | 14.46 | 11.57 | 10.47 |
| 8449 | $C_2H_5$ | $OC_2H_5$ | $CH_3$ | $CH=CH-CH_3$ | 41.23 | 40.56 | | | 14.42 | 15.20 | 11 | 9.28 |
| 8332 | $C_2H_5$ | $OC_2H_5$ | $CH_3$ | $CH=CH-C_6H_5$ | 50.98 | 52.36 | | | 11.89 | 11.76 | 9.07 | 8.02 |
| 8483 | $C_2H_5$ | $OC_2H_5$ | $CH_3$ | $CH=C(CH_3)_2$ | 43.27 | 42.36 | | | 13.76 | 13.52 | 10.50 | 10.12 |
| 5349/40 | $C_2H_5$ | $OC_2H_5$ | $C_2H_5$ | $CH=CCl_2$ | 33.34 | 33.07 | | | 11.66 | 11.3 | 8.9 | 7.5 |
| 8499 | $CH_3$ | $OCH_3$ | $CH(CH_3)_2$ | $CH=CCl_2$ | 31.22 | 30.83 | | | 12.13 | 12.89 | 9.26 | 8.58 |
| 8450 | $C_2H_5$ | $OC_2H_5$ | $CH(CH_3)_2$ | $CH=CCl_2$ | 35.30 | 34.35 | | | 11.22 | 10.85 | 8.13 | 8.29 |
| 8500 | $n-C_3H_7$ | $O-n-C_3H_7$ | $CH(CH_3)_2$ | $CH=CCl_2$ | 38.81 | 38.13 | | | 10.44 | 10.14 | 7.97 | 7.70 |
| 8477 | $CH_3$ | $OCH_3$ | $(CH_2)_3-CH_3$ | $CH=CCl_2$ | 33.34 | 33.68 | | | 11.66 | 11.57 | 8.90 | 7.98 |
| 8474 | $C_2H_5$ | $OC_2H_5$ | $(CH_2)_3-CH_3$ | $CH=CCl_2$ | 37.12 | 35.54 | | | 10.82 | 10.57 | 8.26 | 7.63 |
| 8475 | $n-C_3H_7$ | $O-n-C_3H_7$ | $(CH_2)_3-CH_3$ | $CH=CCl_2$ | 40.38 | 39.28 | | | 10.09 | 10.00 | 7.70 | 7.34 |
| 8497 | $C_2H_5$ | $OC_2H_5$ | $(CH_2)_3-CH_3$ | $CH=CH-CH_3$ | 46.83 | 45.79 | | | 12.60 | 11.76 | 9.62 | 9.28 |
| 8498 | $C_2H_5$ | $OC_2H_5$ | $CH_2-CH(CH_3)_2$ | $CH=CCl$ | 37.12 | 36.81 | | | 10.82 | 10.72 | 8.26 | 8.23 |
| 8591 | $C_2H_5$ | $OC_2H_5$ | $CH_3$ | $\underset{}{\overset{C_2H_5}{\underset{}{C}}}=CH-C_3H_7$ | 48.40 | 48.73 | | | 12.09 | 12.19 | 9.23 | 8.80 |
| 8549 | $C_2H_5$ | $OC_2H_5$ | $CH_3$ | $\underset{}{\overset{Br}{\underset{}{C}}}=CH-CH_3$ | 32.44 | 32.65 | | | 11.55 | 11.42 | 8.66 | 8.30 |
| 8634 | $C_2H_5$ | $OC_2H_5$ | $CH_3$ | $\underset{}{\overset{Cl}{\underset{}{C}}}=CH-CH_3$ | 36.87 | 37.2 | | | 12.90 | 12.84 | 9.84 | 9.06 |
| 8764 | $C_2H_5$ | $OC_2H_5$ | $CH_2-CH=CH_2$ | $CH=CCl_2$ | 35.49 | 34.65 | 4.33 | 4.15 | 11.29 | 11.00 | 8.61 | 7.89 |
| 8805 | $C_2H_5$ | $OC_2H_5$ | $CH_3$ | $CH=C(Cl)SCH_3$ | 33.56 | 36.24 | 4.78 | 4.96 | 11.74 | 11.96 | 17.92 | 17.13 |
| 8825 | $C_2H_5$ | $OC_2H_5$ | $CH_3$ | $CH=C(SCH_3)_2$ | 35.76 | 37.63 | 5.46 | 5.74 | 11.37 | 11.85 | 26.04 | 25.37 |
| 8827 | $C_2H_5$ | $OC_2H_5$ | $CH_2-C_6H_5$ | $CH=CCl_2$ | 42.66 | 41.82 | 4.29 | 4.13 | 9.95 | 9.43 | 7.59 | 7.05 |
| 8828 | $C_2H_5$ | $OC_2H_5$ | $CH_2-C\equiv CH$ | $CH=CCl_2$ | 35.69 | 35.97 | 3.81 | 3.88 | 11.35 | 11.58 | 8.66 | 7.30 |
| 9137 | $C_2H_5$ | $OC_2H_5$ | $CH(CH_3)_2$ | $CH=CH-CH_3$ | 45.12 | 44.51 | 6.94 | 6.60 | 13.15 | 13.07 | 8.10 | 8.24 |
| 9141 | $C_2H_5$ | $OC_2H_5$ | $C_2H_5$ | $\underset{}{\overset{CH_3}{\underset{}{C}}}=CCl_2$ | 35.30 | 36.53 | 4.85 | 4.98 | 11.23 | 11.51 | 8.57 | 8.22 |
| 9579 | $C_2H_5$ | $C_6H_5$ | $CH_3$ | $CH=CCl_2$ | 41.28 | 39.52 | 3.73 | 3.81 | 11.11 | 10.79 | 8.47 | 8.96 |
| 9643 | $C_2H_5$ | $N(CH_3)_2$ | $CH_3$ | $CH=CCl_2$ | 31.31 | 30.71 | 4.38 | 4.25 | 16.23 | 15.70 | 9.29 | 9.15 |
| 9750 | $C_2H_5$ | $OCH_3$ | $CH_3$ | $CH=CCl_2$ | 28.94 | 28.36 | 3.64 | 3.47 | 12.65 | 12.36 | 9.60 | 8.82 |
| 9830 | $C_2H_5$ | $OCH_3$ | $(CH_2)_3-CH_3$ | $CH=CCl_2$ | 35.30 | 34.36 | 4.84 | 4.58 | 11.22 | 10.65 | 8.56 | 7.78 |
| 5338/89 | $C_2H_5$ | $OC_2H_5$ | $CH_3$ | cyclohexenyl-Cl | 42.67 | 40.93 | 5.78 | 5.39 | 11.48 | 11.21 | 8.76 | 8.20 |

The compounds of this invention are endowed with a wide action spectrum with respect to numerous species of parasitic arthropods, as clearly evidenced below in TABLE 5. Because of this important property they offer a practical advantage over most known insecticides. Moreover, they are scarcely toxic to warm-blooded animals in spite of their activity against the arthropods. The toxicity values on albino rats by oral administration of some representative compounds of the invention have been reported on Table 3 in comparison with the toxicity of two commercial triazolyl-phosphoric insecticides.

By the data reported on Table 3 it appears that the $LD_{50}$ of compounds of the present invention is from 10 to 28 times greater than that of Triazophos and Miral ®.

For a still more intensive comparison of the insecticidal activities of the new compounds of the present invention, we have synthesized the compound claimed in U.S. Pat. No. 3,689,500, also endowed with a low toxicity towards mammals. Of this material (M 8172) we have estimated the effects on various arthropods at decreasing doses, together with effects shown by a representative compound of the class described by us in this invention (M 8174). The results, recorded below in TABLE 4, indicate a significantly better activity of compound M 8174 on representative species of the orders of orthoptera, lepidoptera, coleoptera, diptera as well as against nematoda and acari, especially at lower dosages.

From the results reported in TABLES 4 and 5, it is evident that the compounds of the present invention are very effective as insecticides against orthoptera, aphides, diptera, coleoptera, lepidoptera as well as being effective as acaricides and nematocides. Morevoer they are far less toxic toward warm-blooded animals than Triazophos and Miral ® (cf. Table 3).

TABLE 3

Mortality % ge on rat (administered by mouth) at the indicated doses.

| Compounds | Dose mg/kg | Mortality % ge |
| --- | --- | --- |
| M 7852 (mixture, see Table 2) | 800 | 0 |
| M 8634 | 1,400 | 50 |
| M 8549 | 1,000 | 50 |
| M 8174 | 1,600 | 50 |
| M 8550 | 1,700 | 50 |
| M 8560 | 1,200 | 50 |
| Triazophos (reference compound) | 82 | 50 |
| Miral ® (reference compound) | 60 | 50 |

TABLE 4

| | | % ge of activity on various parasites at the indicated doses: | | | | | | | | | | | |
| --- | --- | --- | --- | --- | --- | --- | --- | --- | --- | --- | --- | --- | --- |
| | | Blatta o. | | Spodoptera l. | | Leptinotarsa d. | | Culex p. | | Meloidogyne i. | Tetranycus u. (ad.) | | Hylemyia b. |
| Test Compound | Dose: | 0,1 g/m² | 0,01 g/m² | 0,1‰ | 0,05‰ | 0,1‰ | 0,05‰ | 0,2 ppm | 0,02 ppm | 20 ppm | 0,01‰ | 0,005‰ | 10 ppm | 2 ppm |
| M 8174 | | 100 | 100 | 100 | 90 | 100 | 100 | 100 | 100 | 100 | 100 | 100 | 100 | 100 |
| O,O-diethyl-0-[1-methyl-3-phenyl-1,2,4-triazolyl(5)]-thiophosphate. (Reference compound, U.S. Pat. No. 3,689,500) (M 8172) | | 100 | 20 | 100 | 15 | 92 | 10 | 100 | 0 | 40 | 96 | 76 | 98 | 48 |

TABLE 5

Activity of some of the compounds listed in Table 2 against various species of parasites, at the indicated doses (Legenda: ++ = 100% of mortality, + = 70-99% of mort., ± = 10-69% of mort., − = 0-9% of mort.)

| Test: dose Compound M | Blatta O. 0.01 g/m² | Blatta O. 1 g/m² | Pieris B. 1‰ | Pieris B. 0.01‰ | Spodoptera L. 1‰ | Spodoptera L. 0.05‰ | Leptinotarsa D. 1‰ | Leptinotarsa D. 0.05‰ | Tetranychus U. (adults) 1‰ | Tetranychus U. (adults) 0.01‰ | Culex P. (larvae) 2 ppm | Culex P. (larvae) 0.02 ppm | Culex P. (adults) 0.2 g/m² | Tetranychus U. (eggs) 1‰ | Macrosiphum E. 0.1‰ | Meloidogine I. 100 ppm | Hylemyia S. 50 ppm | Locusta M. 0.2‰ |
|---|---|---|---|---|---|---|---|---|---|---|---|---|---|---|---|---|---|---|
| 7650 | | | ++ | | + | | − | | ++ | | ++ | | | ++ | ± | | | |
| 7853 | ± | | ++ | | ++ | | ++ | | ++ | | ++ | | | ++ | ++ | ± | + | |
| 8086 | | | ++ | | ++ | | ++ | | ++ | | ++ | | | ± | ++ | ++ | ++ | |
| 8167 | | | ++ | | ++ | | ++ | | ++ | | ++ | | | ++ | + | ++ | ++ | |
| 8170 | | | ++ | | ± | | ++ | | ++ | | ++ | | | ++ | ± | ± | ± | |
| 8169 | | | ++ | | ++ | | ++ | | ++ | | ++ | | | ++ | ++ | + | ++ | |
| 9173 | ++ | | ++ | | ++ | | ++ | | ++ | | ++ | | | ++ | ++ | | ++ | |
| 7852 | | | ++ | | ++ | | ++ | | ++ | | ++ | | | ++ | ++ | + | ± | |
| 8089 | ++ | | ++ | | ++ | | ++ | | ++ | | ++ | | | ++ | ++ | ++ | ++ | |
| 8174 | ++ | | | | | | | | | | | | | | | | | |
| 8476 | ++ | | | ++ | | ++ | | ++ | ++ | ++ | ++ | ++ | ++ | | | | | ++ |
| 8119 | ++ | | | ± | | ± | | + | ++ | ++ | ++ | ± | ++ | | | | | ++ |
| 8483 | + | | | ++ | | ± | | ± | ++ | ++ | ++ | ++ | ++ | | | | | ++ |
| 5349/40 | ± | | | ++ | | ++ | | ++ | ++ | ++ | ++ | ++ | ++ | | | | | ++ |
| 8499 | + | | | ++ | | ++ | | ± | ++ | ++ | ++ | ++ | ++ | | | | | ++ |
| 8450 | ± | | | ++ | | ++ | | ++ | ++ | ± | ++ | ++ | ++ | | | | | +++ |
| 8498 | + | | | ++ | | + | | ++ | ++ | ± | ++ | ± | + | | | | | |
| 8497 | − | | | ± | | ± | | ± | ++ | − | ++ | ± | − | | | | | +  |
| 8474 | ± | | | ± | | ± | | ± | ++ | + | ++ | + | − | | | | | |
| Ref. Comp. (U.S. Pat. No.) 3,689,500 (M 8172) | | | | | | | | | | | | | | | | | | |
| 7480 | | | | | | | | | | | | | | | | | | |
| 8084 | | | ± | | ± | | ± | | ++ | ± | ± | | ± | ± | ± | ± | ± | |
| 8171 | ++ | | ++ | ++ | ++ | ++ | ++ | ++ | ++ | ++ | ++ | ++ | ± | ++ | ± | ± | | + |
| 8257 | ++ | | ++ | ++ | ++ | ++ | ++ | ++ | ++ | ++ | ++ | ++ | ++ | ++ | ++ | ++ | ++ | ++ |
| 8261 | ++ | | ++ | + | ++ | + | ++ | ++ | ++ | ++ | ++ | ++ | ++ | ++ | ++ | ++ | ++ | ++ |
| 8308 | ++ | | ++ | ± | ++ | + | ++ | ++ | ++ | ++ | ++ | ± | ++ | ++ | ++ | ± | ++ | ± |
| 8550 | ++ | | ++ | ± | ++ | ± | ++ | ++ | ++ | ± | ++ | ++ | ++ | ++ | ++ | ++ | ++ | ± |
| 8559 | ++ | | ++ | ± | ++ | ± | ++ | ± | ++ | ± | ++ | ++ | ± | ± | ++ | ++ | ± | ++ |
| 8560 | ++ | | ++ | ++ | ++ | ++ | ++ | ++ | ++ | ++ | ++ | ± | ++ | ++ | ++ | ++ | ++ | ++ |
| 8448 | − | | ++ | ± | ++ | ± | ++ | ± | ++ | ± | ++ | ++ | ++ | ++ | ++ | ++ | ++ | + |
| 8593 | ++ | | ++ | ± | ++ | ± | ++ | ± | ++ | ± | ++ | ± | ± | ++ | ++ | ± | ± | ± |
| 8592 | ++ | | ++ | | ++ | | ++ | ++ | ++ | ++ | ++ | ++ | ++ | ++ | ++ | ++ | ± | ++ |
| 8332 | ± | | ++ | ± | ++ | ± | ++ | ++ | ± | ± | ++ | ± | ± | ± | ++ | ++ | | + |
| 8500 | ++ | | ++ | | ++ | | ++ | ++ | ++ | ++ | ++ | ± | ± | ++ | ++ | ++ | | ± |
| 8477 | ++ | | ++ | ± | ++ | ± | ++ | ++ | ++ | ++ | ++ | ± | ± | ++ | ++ | + | ± | ++ |
| 8591 | ++ | | ++ | | ++ | | ++ | ++ | ++ | ++ | ++ | ++ | ± | ++ | ++ | ++ | ± | ++ |
| 8549 | ± | | ++ | − | ++ | ± | ++ | ++ | ++ | + | ++ | ± | ++ | ++ | ++ | ++ | ++ | ± |
| 8634 | ± | | ++ | | ++ | | ++ | ++ | ++ | ++ | ++ | | ++ | ++ | ++ | + | ± | ++ |
| 8764 | ± | | ++ | ± | ++ | ± | ++ | ++ | ++ | ± | ++ | | ++ | ++ | ++ | ++ | ++ | ++ |
| 8805 | ± | | ++ | − | ++ | ± | ++ | ++ | ++ | ++ | ++ | | ++ | ++ | ++ | ++ | ++ | ++ |
| 8825 | ± | | ++ | | ++ | ± | ++ | ++ | ++ | ++ | ++ | | ++ | ++ | ++ | ++ | ++ | + |

TABLE 5-continued

Activity of some of the compounds listed in Table 2 against various species of parasites, at the indicated doses (Legenda: ++ = 100% of mortality, + = 70–99% of mort., ± = 10–69% of mort., − = 0–9% of mort.)

| Test: dose Compound M | Blatta O. 1 g/m² | Blatta O. 0.01 g/m² | Pieris B. 0.01‰ | Spodoptera L. 1‰ | Spodoptera L. 0.05‰ | Leptinotarsa D. 1‰ | Leptinotarsa D. 0.05‰ | Tetranychus U. (adults) 1‰ | Tetranychus U. (adults) 0.01‰ | Culex P. (larvae) 2 ppm | Culex P. (larvae) 0.02 ppm | Culex P. (adults) 0.2 g/m² | Tetranychus U. (eggs) 1‰ | Macrosiphum E. 0.1‰ | Meloidogyne I. 100 ppm | Hylemyia S. 50 ppm | Locusta M. 0.2‰ |
|---|---|---|---|---|---|---|---|---|---|---|---|---|---|---|---|---|---|
| 8827 | ++ | | | | | ++ | | ++ | | ++ | | | ++ | + | ± | | |
| 8828 | ++ | ± | ++ | | | ++ | | ++ | ± | ++ | ± | ± | ++ | ++ | ++ | | ++ |
| 9137 | ++ | | ++ | | | ++ | ++ | ++ | ++ | ++ | | ++ | ++ | ++ | ++ | | |
| 9141 | ++ | | ++ | ++ | | ++ | ++ | ++ | ± | ++ | | ++ | ++ | ± | + | | ++ |
| 9579 | | | | | | | | | | | | | | | | | |
| 9643 | | | | ++ | | | | ++ | | ++ | | | ++ | + | | | |
| 9750 | ++ | ++ | ++ | ++ | ++ | ++ | ± | ++ | ++ | ++ | ++ | ++ | ++ | ++ | | | |
| 5338/89 | ++ | | ++ | ++ | | ++ | ± | ++ | + | ++ | | ++ | ++ | ± | | | |
| 8475 | − | | | ± | | | | ± | | | | | | ± | + | | ± |

In order still better to illustrate the present invention a number of examples are given below.

EXAMPLE 1

Preparation of 1-phenyl-3-acetyl-1,2,4-triazole(5)-one:

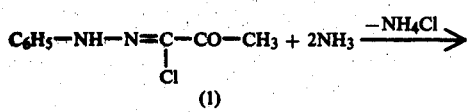

(1)

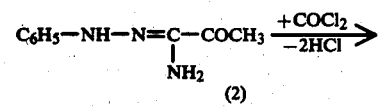

(2)

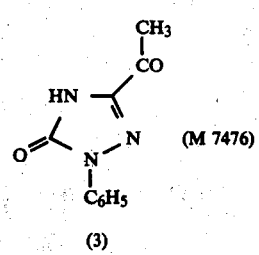

(M 7476)

(3)

80 ml of an aqueous solution of NH₃ (32% b.w.) (1.32 moles) were admixed with 500 ml of ethanol. To this solution 60 g (0.305 moles) of α-chloro-α-acetyl-formylidene-phenylhydrazine (1), were added in small portions. Once the addition was accomplished, the mixture was stirred for 2 hours at room temperature. The insoluble α-amino-α-acetyl-formylidene-phenylhydrazine (2) (48 g) was filtered and washed with 200 ml of water (yellow solid, m.p. 182°–184° C.).

42.5 g (0.24 moles) of α-amino-α-acetyl-formylidene-phenylhydrazine were suspended in 300 ml of benzene. To the suspension were added 57 ml (0.72 moles) of pyridine and then, dropwise, 40 ml of a benzenic solution of COCl₂ at 10% concentration (% b. vol.: 0.36 moles), while maintaining the temperature at 15°–20° C.

Once the addition had been accomplished, the mixture was stirred for 30 minutes at room temperature, and then 100 ml of H₂O and 10 ml of concentrated HCl were added to it. The whole was stirred for 2 hours at room temperature. The insoluble material was filtered on a porous diaphragm and washed with H₂O.

25 g of 1-phenyl-3-acetyl-1,2,4-triazole (5)-one(3) were obtained. (m.p. 174°–176° C.).

EXAMPLES 2–4

By operating as described in Example 1:
starting from α-chloro-α-benzoyl-formylidene-phenylhydrazine, 1-phenyl-3-benzoyl-1,2,4-triazole (5)-one was prepared

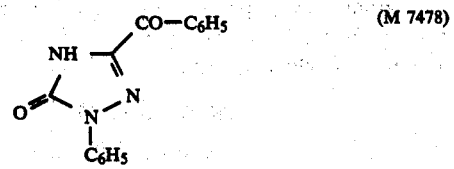

(M 7478)

starting from α-chloro-α-methylthio-acetyl-formylidene-phenylhydrazine, 1-phenyl-3-(methylthio-acetyl)-1,2,4-triazole(5)-one was prepared:

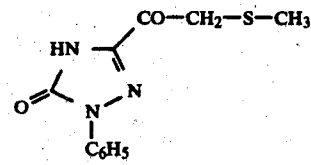

(M 8269)

starting from α-chloro-α-carboethoxy-formylidene-phenylhydrazine, 1-phenyl-3-(carboxyethyl)-1,2,4-triazole(5)-one was prepared:

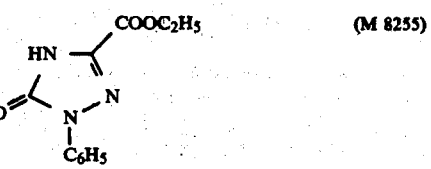

(M 8255)

EXAMPLE 5

Reaction:

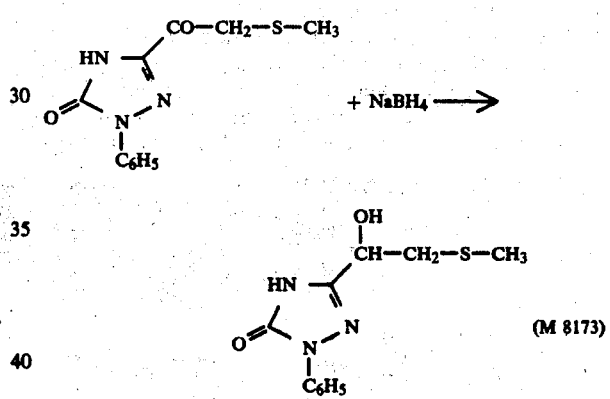

(M 8173)

2.3 g of 1-phenyl-3-methylthioacetyl-1,2,4-triazole(5)-one, suspended in 40 ml of methanol, were treated dropwise with a solution of 0.3 g of NaBH₄ in 5 ml of water. The reaction mixture was stirred for 1 hour, then was additioned with 0.5 ml of concentrated HCl and the solvent removed.

The residue was collected with 20 ml of water and 0.5 ml of concentrated HCl, the aqueous solution was extracted with ethyl acetate (3+30 ml) and the organic phase was dried with anhydrous Na₂SO₄.

The solvent was removed in vacuum and the solid residue, crystallized from benzene (10 ml), yielded 1 gram of 1-phenyl-3-(1-hydroxy-2-methyl-mercapto)-ethyl-1,2,4-triazole(5)-one (ivory colored solid, m.p.=102°–104° C.). (M 8173).

EXAMPLE 6

Operating in the same way as described above in Example 5, but starting from 70 g of 1-phenyl-3-acetyl-1,2,4-triazole(5)-one, 56 g of 1-phenyl-3-(1-hydroxyethyl)-1,2,4-triazole(5)-one were obtained (m.p.=149°–150° C.).

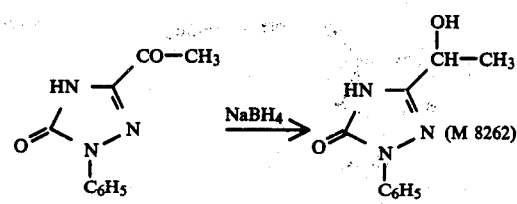

EXAMPLE 7

To 16 g of the product obtained as described in the preceding Example 6, dissolved in 350 ml of CHCl₃, 7.6 ml of SOCl₂ were added dropwise, under stirring.

The solution was stirred at room temperature for 2 hours, and then poured into 150 ml of water. The chloroformic phase was separated and dried. After removal of the solvent, 17 g of 1-phenyl-3-(1-chloroethyl)-1,2,4-triazole(5)-one were obtained (m.p.=159°–160° C.). (M 8085).

5.5 g of the last-mentioned product thus obtained, dissolved in 150 ml of benzene, were dehydrochlorinated by slightly refluxing in the presence of 7.5 g of triethylamine. Once the reaction was accomplished, 40 ml of water and 10 ml of concentrated HCl were added to the reaction mixture.

The benzenic phase was separated, washed with water and dried with anhydrous Na₂SO₄. The solvent was removed in vacuum up to a volume reaching 50 ml. By slight cooling, 2 g of 1-phenyl-3-vinyl-1,2,4-triazole(5)-one were separated (m.p. 200° C.). (M 8263).

EXAMPLE 8

Preparation of 1-methyl-3-tribromovinyl-1,2,4-triazole (5)-one and 1-methyl-3-(α-bromo-β,β-dichlorovinyl)-1,2,4-triazole (5)-one.

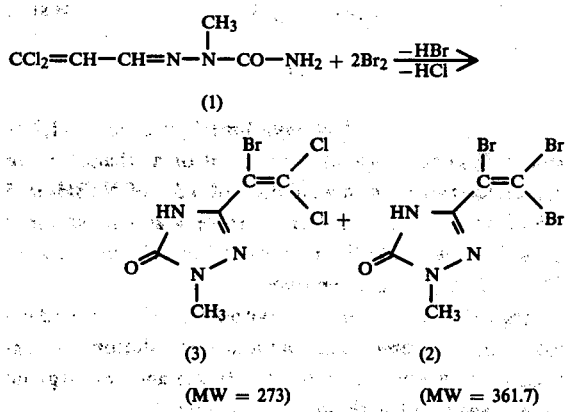

3 g (0.0153 moles) of 1-(β,β-dichloroacrylidene)-2-methyl-semicarbazide (1) were dissolved in 15 ml of glacial acetic acid, and then 1.6 ml of bromine (0.031 moles) were slowly added to this solution. The mixture was then heated (with slight reflux) for 30 minutes, and then it was cooled and 150 ml of H₂O were added. It was then extracted with ethyl acetate (50 ml two times). The ethyl acetate solution was washed with 50 ml of H₂O and with a saturated solution of NaHCO₃ (40 ml three times). Then it was dried with anhydrous Na₂SO₄, filtered, and the solvent evaporated.

The residue was recovered with 50 ml of 10% aqueous NaOH and the whole heated up to incipient boiling. Thereupon the mixture was cooled and filtered. The filtrate was acidified with concentrated HCl. A yellowish solid separated which was extracted with ethyl acetate (2×50 ml).

The organic solution was then washed with water (50 ml), dried with anhydrous Na₂SO₄, and the solvent removed. 1.9 g of a yellowish solid were obtained which crystallized from benzene (30 ml), yielded 1 gram of an almost white crystalline solid (m.p.=161°–163° C.).

This solid consists of a mixture of compounds (2) and (3), as evidenced by its mass spectrum in which two molecular peaks of almost equal intensity are present [(2): M⁺=361.7, (3): M⁺=273]. From the data upon elemental analysis, it was calculated that the mixture is composed of 56% of compound (3) and 44% of compound (2).

EXAMPLE 9

Preparation of 1-methyl-3-(β,β-dichlorovinyl)-1,2,4-triazole(5)-one:

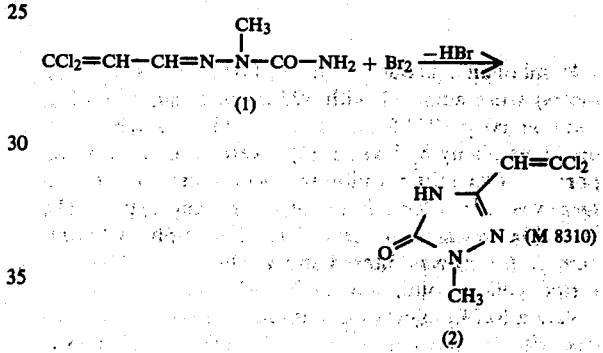

9.7 g (0.0494 moles) of 1-(β,β-dichloroacrylidene)-2-methyl-semicarbazide (1) were dissolved in 50 ml of glacial acid. The solution was slightly refluxed while 2.8 ml (0.054 moles) of bromine were very slowly added dropwise. On completion of the dropwise addition, the solution was allowed to cool down spontaneously.

The acetic acid solution was slowly added dropwise to a suspension of 120 g of NaHCO₃ in 300 ml of H₂O. Once the effervescence had subsided, 250 ml of ethyl acetate were added and the whole was stirred.

The organic phase was separated, dried with anhydrous Na₂SO₄ and the solvent evaporated. When the volume had been reduced to 40 ml, the evaporation was interrupted and the solution was cooled down to about 0° C. The yellowish precipitate was filtered on a porous diaphgram.

2 grams of 1-methyl-3-(β,β-dichlorovinyl)-1,2,4-triazole (5)-one (2) were obtained (m.p. =215°–216° C. after re-crystallization from ethyl acetate).

EXAMPLES 10–11

Starting from the appropriate 1-(polyhaloacrylidene)-2-methyl-semicarbazide and proceeding as described above in Example 9, the following 1,2,4-triazole-(5)-ones were prepared:

1-methyl-3-(β,β-dibromovinyl)-1,2,4-triazol-(5)-one

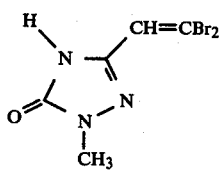

1-methyl-3-(tribomovinyl)-1,2,4-triazol-(5)-one

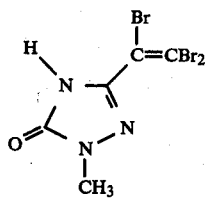

EXAMPLE 12

Preparation of 1-methyl-3-($\beta,\beta$-dichlorovinyl)-1,2,4-triazol-(5)-one by using ferric chloride:

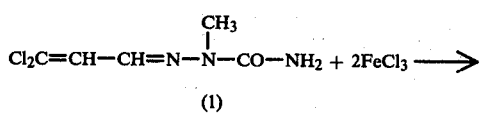

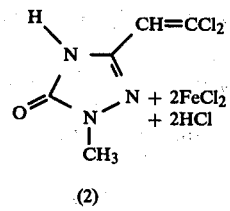

A solution of 49 g (0.18 moles) of hexahydrated ferric chloride (FeCl$_3$.6H$_2$O), in 100 ml of water, was added to a solution of 17.5 g (0.089 moles) of 1-($\beta,\beta$-dichloroacrylidene)-2-methylsemicarbazide (1) in acetic acid (50 ml). The resulting solution was heated at reflux temperature for 3½ hours, and then left to cool spontaneously following which it was additioned with 150 ml of water. The solution was then cooled at about 0° C. (water and ice bath).

12 g of 1-methyl-3-($\beta,\beta$-dichlorovinyl)-1,2,4-triazole-5-one (2) precipitated (m.p.=215°-216° C., crystallized from ethyl acetate).

EXAMPLE 13

Preparation of 1-methyl-3-($\beta,\beta$-dimethylvinyl)-1,2,4-triazol-5-one.

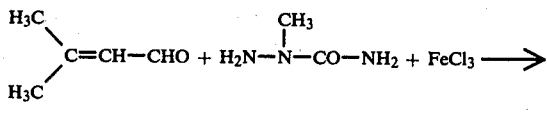

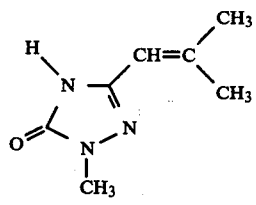

To a solution of 10.6 g (0.119 moles) of 2-methylsemicarbazide (2) in acetic acid (100 ml), 10 g (0.119 moles) of $\beta,\beta$-dimethyl-acrolein (1) were added dropwise. The reaction mixture was stirred at 50° C. for 15 minutes, and then a solution of 64.2 g (0.237 moles) of FeCl$_3$.6H$_2$O in 60 ml of water was added to it. The whole was stirred at 75° C. for 3 hours, and then it was poured into water (400 ml) and extracted with ethyl acetate (2×150 ml). The organic phase was separated, washed with water and with a saturated solution of NaHCO$_3$, and dried with anhydrous Na$_2$SO$_4$.

By removing the solvent, 4 g of 1-methyl-3-($\beta,\beta$-dimethylvinyl)-1,2,4-triazol-5-one (3) were obtained (m.p.−144°-146° C.).

EXAMPLE 14

Preparation of 1-methyl-3-($\beta$-chloro-$\beta$-methoxyvinyl)-1,2,4-triazol-5-one.

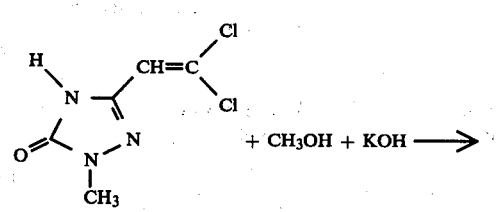

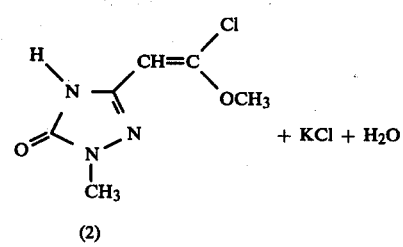

Into a round-bottomed flask fitted with a reflux condenser, 6.8 g (0.035 moles) of 1-methyl-3-($\beta,\beta$-dichlorovinyl)-1,2,-4-triazol-5-one (1), 50 ml of methanol, and 8 g of KOH were introduced. The reaction mixture was stirred at reflux temperature for 5 hours, then poured into water (150 ml) and concentrated HCl (20 ml) and extracted with ethyl acetate (3×100 ml). The organic phase was dried with anhydrous Na$_2$SO$_4$ and the solvent removed.

3 g of 1-methyl-3-($\beta$-chloro-$\beta$-methoxyvinyl)-1,2,4-triazol-5-one (2) were obtained (m.p.=198°-199° C.).

EXAMPLE 15

Preparation of 1-methyl-3-(2-chloro-1-cyclohexenyl)-1,2,4-triazol-5-one:

$$\underset{(1)}{\text{cyclohexenyl}(Cl)-CH=N-N(CH_3)-CO-NH_2} + FeCl_3 \longrightarrow$$

(structure of 1-methyl-3-(2-chloro-1-cyclohexenyl)-1,2,4-triazol-5-one)

To a solution of 27 g (0.1 moles) of FeCl$_3$.6H$_2$O in 30 ml of water, 50 ml of acetic acid were added. The resulting solution was stirred at 100° C. while a solution of 10.8 g (0.05 moles) of the semicarbazone (1) in 50 ml of acetic acid was added dropwise in 2 hours. The heating was maintained for one additional hour, then the solution was cooled, additioned with 300 ml of water, and extracted with chloroform (2×200 ml). The chloroformic extract was separated, washed with a saturated solution of NaHCO$_3$ and dried with anhydrous Na$_2$SO$_4$. By removing the solvent 4.5 g of an oil were obtained. The oil left to stand solidified, and the solid raw substance upon washing with diethyl ether yielded 4 g of 1-methyl-3-(2-chloro-1-cyclohexenyl)-1,2,4-triazol-5-one(3) (m.p.=183°–185° C.). Elemental analysis: Cl theoretical, 16.60%, found, 16.76%.

EXAMPLE 16

Preparation of O,O-diethyl-O-(1-methyl-3-tribromovinyl-5-triazolyl)-thiophosphate:

(reaction scheme: 1-methyl-3-tribromovinyl-5-hydroxy-1,2,4-triazole sodium salt (1) + Cl–P(S)(OC$_2$H$_5$)$_2$ (2) → product (3), with −NaCl)

3.82 g (0.01 moles) of 1-methyl-3-tribromovinyl-5-hydroxy-1,2,4-triazole (1) (sodium salt) were dissolved in 100 ml of acetone. To this solution were added 1.6 ml (0.01 moles) of O,O-diethyl-chlorothiophosphate (2). The solution was then heated to 55°–60° C. for 2 hours. Thereupon the acetone was evaporated and the residue was collected with 100 ml of diethyl ether and 50 ml of H$_2$O. The whole was then stirred. The organic phase was separated, dried with anhydrous Na$_2$SO$_4$ and the solvent evaporated. Thereby were obtained 4.7 g of a yellow oil, which was purified by chromatography on silica gel, using benzene as an eluent: yield 3.5 g of O,O-diethyl-O-(1-methyl-3-tribromovinyl-5-triazolyl)-thiophosphate (3): (white solid m.p.=45°–50° ).

In a similar way the other O,O-diethyl-O-triazolyl-thiophosphates reported in TABLE 2 were prepared.

EXAMPLE 17

By operating as described in Example 16, but starting from 1-methyl-3-($\beta,\beta$-dichlorovinyl)-5-hydroxy-1,2,4-triazole (sodium salt) and from O,O-dimethyl-chlorothiophosphate, the O,O-dimethyl-thiophosphoric ester of 1-methyl-3-($\beta,\beta$-dichlorovinyl)-5-hydroxy-1,2,4-triazole was prepared (M 8373), (m.p.=102°–103° C.). Elemental analysis: Cl (theor.): 22.30%; (found): 22.45%.

EXAMPLE 18

An investigation of the biological activities of the compounds of the present invention was made as follows:

(1) Biological activity on *Macrosiphum euphorbiae* (Aphides)

Potato plants grown in pots were infested with adult females of aphides and, after several hours, were sprinked with an aqueous dispersion of the products under examination (see TABLE 5).

The percentage of mortality was assessed after 24 hours after the treatment (untreated plants=0).

(2) Biological activity on *Pieris brassicae* (Lepidotera)

Cut-off cauliflower leaves were sprinkled with an aqueous dispersion of the products under examination (see TABLE 5).

After drying, the leaves were infested with 5-day old larvae. The percentage of mortality of the larvae (untreated leaves=0) was determined after 48 hours from treatment.

(3) Biological activity on *Leptinotarsa decemlineata* (Coleoptera)

Small potato plants grown in pots were infested with 4-day old larvae, and were then sprinkled with an aqueous dispersion of the products under examination (see Tables 4 and 5).

The mortality percentage (untreated small plants=0) was determined after 48 hours from treatment.

(4) Biological activity on *Culex pipiens* (Diptera)

Into glasses containing an aqueous dispersion of the products under examination (see Tables 4 and 5) there were introduced mosquito larvae of third and fourth age.

The mortality percentage of the larvae (glasses containing pure water=0) was determined after 24 hours from treatment.

(5) Biological activity on adults of *Tetranychus urticae* (Acari)

Discs of bean leaves were infested with adult acari and then sprinkled with an aqueous dispersion of the products under examination (see Tables 4 and 5).

The mortality percentage was determined after 24 hours from treatment (untreated leaf discs, mortality=0).

(6) Biological activity on *Tetranychus urticae* (Acari)

Small discs of bean leaves were infested with Acari eggs and were then sprinkled with an aqueous dispersion of the products under examination (see Table 5).

The mortality percentage was determined after 6 days from treatment (untreated leaf discs, mortality=0).

(7) Biological activity on *Spodoptera littoralis* (Lepidoptera)

Cut tobacco leaves were sprinkled with an aqueous dispersion of the products under examination (see Tables 4 and 5).

After drying, the leaves were infested with 5-day old larvae.

The percentage of mortality of the larvae was determined after 48 hours from treatment (untreated leaves, mortality=0).

(8) Biological activity on *Meloidogyne icognita* (Nematoda)

A 1:1 mixture of field soil and sand, infested with newborne larvae and eggs of Nematoda, were treated, by uniform admixing, with an aqueous dispersion of the products under examination (see Tables 4 and 5). The soil was then distributed into plastic pots, and after 5 days in each pot there were planted 5 small tomato plants about 20 cm high.

The results were recorded 21 days after the transplanting. The roots of the plants extracted from the soil were observed in order to ascertain the degree of infestation by counting the galls that had formed.

The nematocidal activity was expressed as the percentage reduction of infestation with respect to the witness (small plants transplanted into a non-treated soil, activity=0).

(9) Biological activity on *Hilemyia brassicae* (Diptera)

Samples of soil were treated by uniform mixing with an aqueous dispersion of the products under examination (see Tables 4 and 5). The soil was then divided into two pots and in each of these 4 small radish plants were transplanted. The plants were subsequently infected by putting to the soil 50 Diptera eggs in the middle of the surface of the pots.

The results were recorded 10 days after treatment by extracting the plants from the soil and by counting the number of larvae present on the roots and on the surrounding soil.

The insecticidal activity was expressed as percentage of reduction of the infestation in comparison with the witness plants (plants transplanted into untreated soil, activity=0).

(10) Biological activity on *Blatta orientalis* (Ortoptera)

The bottom and walls of glass crystallizers were treated uniformly with an acetonic solution of the products under examination (see Tables 4 and 5). After evaporation of the solvent, into each crystallizer were introduced ten 80-100 days old neanides. The crystallizers were then closed with a metal net cover. After 24 hours from the start of the treatment, the insects were transferred to similar untreated crystallizers, and there were appropriately nourished in conventional manner.

The percentage of mortality (untreated insects=0) was determined after 48 hours from the start of the treatment.

What is claimed is:

1. Compounds having the formula

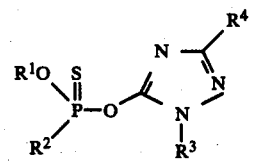

wherein
$R^1$=alkyl with from 1 to 5 carbon atoms;
$R^2$=$OR^1$;
$R^3$=alkyl with from 1 to 5 carbon atoms; and
$R^4$=vinyl, halovinyl, polyhalovinyl, vinyl substituted with phenyl groups, alkyl groups with from 1 to 4 carbon atoms, O-alkyl groups with from 1 to 4 carbon atoms, S-alkyl groups with from 1 to 4 carbon atoms.

2. Compounds according to claim 1 in which $R^4$=vinyl, halovinyl, polyhalovinyl.

3. O,O-diethyl-thiophosphoric ester of 1-methyl-3-β,β-dichlorovinyl)-5-hydroxy-1,2,4-triazole.

4. O,O-diethyl-thiophosphoric ester of 1-methyl-3-trichlorovinyl-5-hydroxy-1,2,4-triazole.

5. O,O-diethyl-thiophosphoric ester of 1-methyl-3-vinyl-5-hydroxy-1,2,4-triazole.

6. O,O-diethyl-thiophosphoric ester of 1-isopropyl-3-(β,β-dichlorovinyl)-5-hydroxy-1,2,4-triazole.

7. O,O-diethyl-thiophosphoric ester of 1-n.butyl-3-(β,β-dichlorovinyl)-5-hydroxy-1,2,4-triazole.

8. O,O-diethyl-thiophosphoric ester of 1-methyl-3-(β,β-dibromovinyl)-5-hydroxy-1,2,4-triazole.

9. O,O-diethylthiophosphoric ester of 1-methyl-3-tribromovinyl-5-hydroxy-1,2,4-triazole.

10. O,O-diethylthiophosphoric ester of 1-methyl-3(α-bromo-β,β-dichlorovinyl-5-hydroxy-1,2,4-triazole in admixture with O,O-diethylthiophosphoric ester of 1-methyl-3-tribromovinyl-5-hydroxy-1,2,4-triazole, in the proportion of about 1:1 by weight.

11. O,O-dimethylthiophosphoric ester of 1-methyl-3-(β,β-dichlorovinyl)-5-hydroxy-1,2,4-triazole.

12. Compounds according to claim 1 in which $R^4$=vinyl substituted with alkyl groups with from 1 to 4 carbon atoms.

13. O,O-diethyl-thiophosphoric ester of 1-methyl-3-(β,β-dimethylvinyl)-5-hydroxy-1,2,4-triazole.

14. O,O-diethyl-thiophosphoric ester of 1-methyl-3-(β-methylvinyl)-5-hydroxy-1,2,4-triazole.

* * * * *